United States Patent [19]

Sato et al.

[11] 4,339,079
[45] Jul. 13, 1982

[54] FRAGRANCE EMITTER

[76] Inventors: Osamu Sato, 3-148-5 Aratacho; Masahiro Shibagaki, 2-3-23 Minatocho, both of Hyogo-ku, Kobe, Japan

[21] Appl. No.: 231,096

[22] Filed: Feb. 3, 1981

[30] Foreign Application Priority Data

Jul. 11, 1980 [JP] Japan .................. 55-98460[U]

[51] Int. Cl.³ .................................. A61L 9/12
[52] U.S. Cl. ........................ 239/43; 239/45; 239/46; 239/49; 239/51; 239/57; 239/59; 422/123; 422/306
[58] Field of Search ............ 422/123, 306; 239/38, 239/43, 45, 46, 49, 51, 57, 59

[56] References Cited

U.S. PATENT DOCUMENTS

| 1,818,684 | 8/1931 | Blechman | 239/52 X |
| 2,991,517 | 7/1961 | Bundy | 422/123 |
| 3,482,929 | 12/1969 | Gentil | 239/49 X |
| 3,754,707 | 8/1973 | Morane | 239/59 |
| 3,848,803 | 11/1974 | Levey | 239/59 |
| 4,067,692 | 1/1978 | Parrls | 239/59 X |
| 4,161,284 | 7/1979 | Rattan | 239/43 |
| 4,229,415 | 10/1980 | Bryson | 239/57 X |

FOREIGN PATENT DOCUMENTS 1544410 4/1979 United Kingdom ............... 422/123

Primary Examiner—Barry S. Richman
Attorney, Agent, or Firm—Merriam, Marshall & Bicknell

[57] ABSTRACT

A device for producing a pleasant or fragrant scent in a room or automobile, for example. The device includes a housing that encloses a container of a fragrant liquid. At least part of the container is made of a substantially transparent material that can also be pierced by a needle or sharp pin. The container includes a reservoir part that is visible through an opening formed in the housing, so that a user may check the amount of liquid remaining in the container. The container further includes a chamber part that may be pierced so that the liquid seeps from it, and a pad or layer of material absorbs the seepage. An adjustable window formed on the housing controls the amount of the liquid that evaporates from the absorbent layer.

4 Claims, 4 Drawing Figures

FIG. 4
FIG. 3
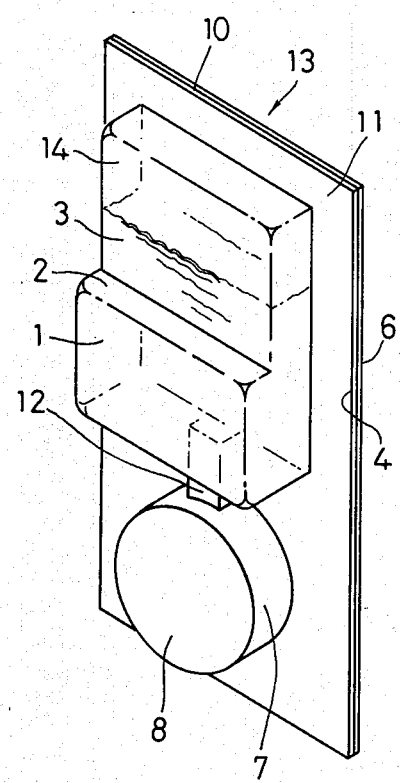
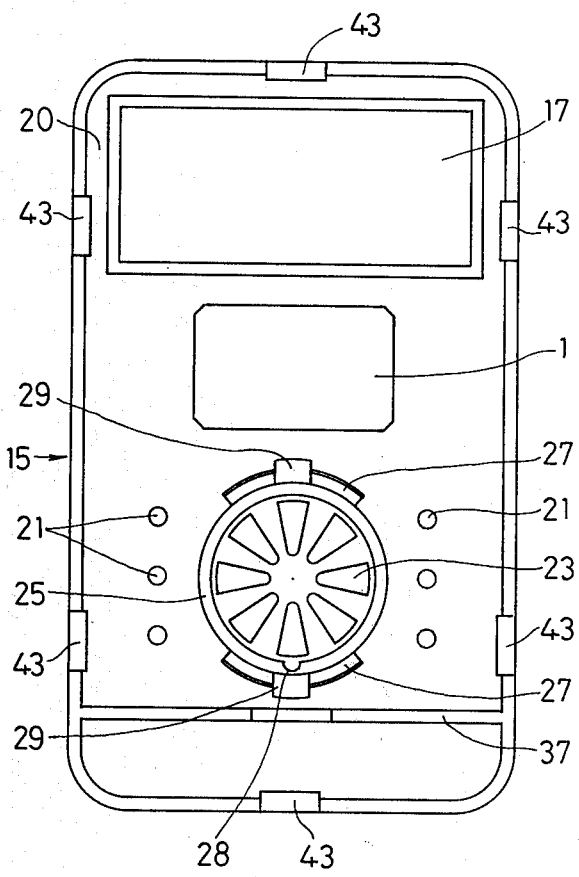

FRAGRANCE EMITTER

The present invention relates to a device for emitting a refreshing fragrance or scent.

Devices for producing such a scent or fragrance are well known, and have been extensively used indoors and in cars. However, some devices of this character have been complicated in structure and therefore inconvenient to handle. In other devices of this type, the enclosed fragrance-producing material is quickly depleted or consumed and it generates a strong fragrance for a short time. Furthermore, prior devices have not been refillable, and therefore in order to maintain the emission of fragrance for a long period of time, it has been necessary to replace the entire device.

It is a general object of this invention to provide an economically constructed device which is able to generate a weak fragrance over a relatively long time and which can be used semipermanently by replacing a container of fragrance-producing liquid.

A device in accordance with this invention comprises a container of fragrant liquid, the container including a reservoir having a transparent or semitransparent front wall and a chamber which communicates with the reservoir and houses a liquid-absorbing material, the chamber having a semi-rigid front wall which can be pierced by a needle or sharp pin; a housing which encloses the container and has an opening through which the front wall of the reservoir is exposed, and at least one window positioned in front of the chamber, the open area of the window being variable; and an evaporation sheet which is interposed between the window and the front wall of the chamber, the sheet absorbing the liquid.

A preferred embodiment of the invention is described in detail by way of a specific example, with reference to the accompanying drawings, wherein:

FIG. 3 is a back view of the interior of a housing part of the device; and

FIG. 4 is a perspective view of the container of the device.

Figure 1:
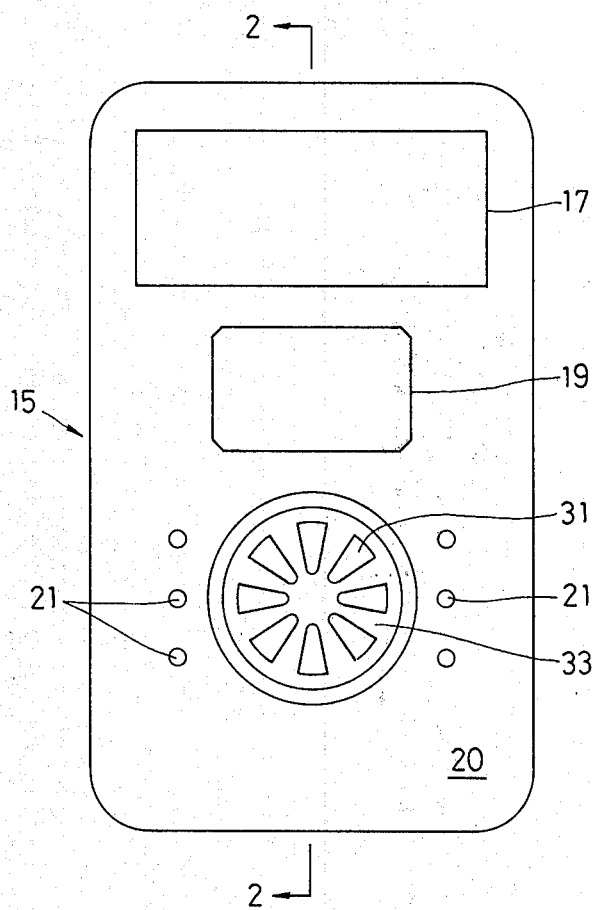
FIG. 1 is a front elevational view of a device in accordance with this invention.

While the following detailed description includes references to the locations of parts relative to other parts in a figure of the drawings, such as above or below, it will be understood that such references are used only to facilitate the description of the parts, since the apparatus described may have various orientations before and during use.

With reference to the drawings, the device comprises an outer housing 15 and a container or enclosure 13 mounted within the housing 15. The container 13 (FIGS. 2 and 4) is made, for example, of a molded plastic member 4 and a plain flat plastic sheet 6 which are fused together at their periphery 11. The parts 4 and 6 are transparent and semirigid and can be pierced by a needle or pin (not shown). The container 13 includes a hollow liquid reservoir portion having an upward extension 3 that is thinner than the reservoir 1 and thus forms a step 2. The container 13 further includes a cylindrical bottom chamber 7 that is positioned below the reservoir 1 and has a flat front wall 8, the chamber 7 being connected with the reservoir 1 through a narrow passage 12.

The bottom chamber 7 is loaded or filled with a spongy liquid-absorbent member 9 (FIG. 2) having roughly the same shape as the chamber 7. The container 13 is substantially filled with a concentrated perfume or fragrant liquid 5 and then the two parts 4 and 6 of the enclosure 13 are sealed liquid-tight. If the entire volume of the container 13 were completely filled with the liquid 5 before the periphery 11 is sealed, a portion of the liquid 5 might leak out through the periphery during the sealing operation. In order to avoid such leakage, the container 13 should be filled with such an amount of the liquid 5 that an amount of air 14 remains above the liquid level within the upward extension 3 when the container 13 is upright. More specifically, the entire periphery 11 may be sealed except for the portion 10 (FIGS. 2 and 4) along the upper side of the extension 3. The container is then filled with the liquid 5 through the portion 10 while the container is positioned in an upright position (FIG. 4), and then the portion 10 is sealed shut.

Figure 2:
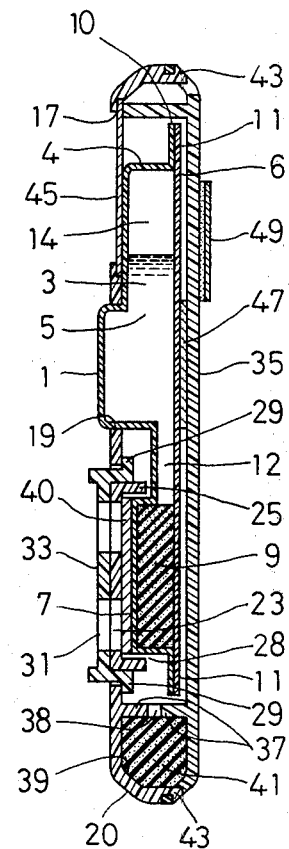
FIG. 2 is a sectional view taken on the line 2—2 of FIG. 1.

The housing 15 includes a front cover 20 and a back or base plate 35 (FIG. 2). These may, for example, be two molded metal or plastic parts that are releasably fastened together by a conventional snap or clip fastener construction 43. The front cover 20 has an upper opening 17 (FIGS. 1 to 3), a middle opening 19 and a number of small lower holes 21, all being formed therethrough. The middle opening 19 is sized and located so as to fit snugly around a front portion of the reservoir 1 as shown in FIG. 2. The cover 20 also has a plurality of windows 23 formed therethrough at angular intervals, below the middle opening 19 and in front of the chamber 7. An annular inward projection 25 (FIG. 3) extends around the windows 23, and a pair of arcuate slots 27 are formed therethrough outside of the projection 25. The projection 25 is sized and located to fit snugly around a front portion of the bottom chamber 7 as shown in FIG. 2. The projection 25 also has an axial groove 28 formed in its inner periphery.

A rotary member or dial 33 (FIGS. 1 and 2) has radial openings 31 formed therethrough which correspond to the radial windows 23 of the cover 20. The member 33 is positioned over the windows 23 and a pair of legs 29 on the member 33 slideably engages within the slots 27. The slots 27 and the legs 29 are on opposite sides of the windows and the slots are substantially wider than the legs 29, so that the rotary member 33 may be rotated on the cover 15 by one's fingers to change the open area of the windows 23. The member 33 may be adjusted from a maximum open position where the windows 23 and 31 overlie, to a maximum closed position where the windows 31 are between the windows 23.

The cover 20 and the base plate 35 each has a lateral inwardly extending partition 37 (FIG. 2) located below the container 13. The partitions 37 are opposed to each other and define a space 39 therebelow when the parts are assembled, the space 39, however, being open at its upper end through a gap 38 remaining between the partitions 37.

A generally circular evaporation sheet 40 (FIG. 2) made of a liquid-absorbent material such as felt is placed within the annular projection 25 and between the chamber 7 and the windows 23 of the cover 20.

The liquid container 13 is housed between the cover 20 and base plate 35, with the front wall of the reservoir exposed by and projecting from the middle opening 19, and with the front portion of the bottom chamber 7 received within the annular projection 25. A spongy liquid-absorbent member 41 is also placed within the bottom space 39.

The cover 20 and base plate 35 are detachably coupled by the previously mentioned fastener or engaging means 43. This enables the evaporation sheet 40 to be tightly fitted between the front side of the bottom chamber 7 and the inside of the cover 20 adjacent the windows 23.

A display panel 45 is preferably placed between the upper opening 17 of the cover 20 and the extension 3 of the reservoir 1, which serves as part of the wall of the cover 20 in front of the extension 3. A decorative plate 47 may be attached to the inside of the base plate 35 at the level of the middle opening 19 to improve the interior appearance of the the base plate 47 when viewed through the reservoir 1.

The device may be attached to a wall by a two-sided adhesive sheet 49 or otherwise suspended.

When in use, the rotary member 33 is manually rotated to open the windows 23. The front wall of the bottom chamber 7 is then pierced at one or more spots as by a pointed needle (not shown) which is inserted through the windows 23 and 31 and the evaporation sheet 40. The liquid 5 impregnated in the sponge 9 then seeps through the needle perforations and into the felt sheet 40, where the liquid gradually evaporates or is emitted through the windows 23 and 31. The liquid 5 is absorbed by the felt sheet 40 very slowly so that the device emits a weak fragrance or scent over a relatively long period of time, and the amount of emission may be adjusted by turning the member 33 in order to vary the open area of the windows 23 and 31. The amount of liquid remaining within the reservoir 1 can be observed through the middle opening 19. The surplus portion of the liquid 5 which cannot evaporate from the sheet 40 will drain through the groove 28 in the projection 25 and through the gap 38 to the sponge 41 which absorbs it. The liquid absorbed by the sponge 41 will then evaporate through the gap 38 and primarily through the small holes 21 in the cover 20.

When the liquid has been consumed, the container 13 may be replaced by disassembling the cover 20 and base plate 35 and replacing the spent container with a fresh one

What is claimed is:

1. A device for emitting a fragrant scent, comprising a container adapted to receive a fragrant liquid, said container including walls forming a front wall and a back wall and said walls forming a reservoir portion and a chamber portion which is below said reservoir portion and an open flow passage between said reservoir portion and said chamber portion allowing for relatively unimpeded flow of liquid between said reservoir and chamber portions, said reservoir and chamber portions and said passage having a single piece construction, a housing which encloses said container therein, said housing having an opening therein which exposes said front wall of said reservoir portion, and said housing further having at least one window adjacent said front wall of said chamber portion, said front wall of said reservoir portion being substantially transparent and said front wall of said chamber portion being pierceable by a needle or pin inserted through said window, a liquid absorbent member filling said chamber portion, an evaporation sheet tightly fitted between said window and said front wall of said chamber portion, the liquid in said chamber portion impregnating said absorbent member and seeping through holes formed by piercing said front wall of said chamber portion, said liquid further seeping into said evaporation sheet and being emitted through said window, and means connected to said housing for varying the size of said window.

2. A device according to claim 1, wherein said housing further includes means forming a bottom space below said container and said evaporation sheet, and an absorbent material within said bottom space.

3. A device according to claim 1, wherein said container further includes an extension portion which is above said reservoir, said extension portion being enclosed and covered by said housing.

4. A device according to claim 3, and further including a fragrant liquid in said container and only partially filling said container up to a liquid level within said extension portion.

* * * * *